United States Patent
Sutter

(10) Patent No.: US 6,343,961 B1
(45) Date of Patent: Feb. 5, 2002

(54) CONNECTING PLUG FOR A MEDICAL BIPOLAR COAGULATION INSTRUMENT

(75) Inventor: Hermann Sutter, Gundelfingen (DE)

(73) Assignee: Select Medizin-Technik Hermann Sutter GmbH, Freiburg (DE)

( * ) Notice: Subject to any disclaimer, the term of this patent is extended or adjusted under 35 U.S.C. 154(b) by 0 days.

(21) Appl. No.: 09/618,327

(22) Filed: Jul. 18, 2000

(30) Foreign Application Priority Data

Jul. 22, 1999 (DE) .......................................... 199 34 532

(51) Int. Cl.[7] .............................................. H01R 13/42
(52) U.S. Cl. ............................ 439/737; 606/50; 606/51
(58) Field of Search ............................. 439/737, 733.1, 439/752, 695; 606/50, 51

(56) References Cited

U.S. PATENT DOCUMENTS

| | | | |
|---|---|---|---|
| 1,071,978 A | | 9/1913 | White |
| 2,429,039 A | * | 10/1947 | Warner .................. 219/85.14 |
| 2,636,971 A | * | 4/1953 | Delbrook .................. 219/233 |
| 3,122,407 A | * | 2/1964 | Cowe ......................... 439/740 |
| 5,605,478 A | * | 2/1997 | Woodard .................. 439/695 |
| 5,925,046 A | * | 7/1999 | Vogel et al. .................. 606/51 |

FOREIGN PATENT DOCUMENTS

| | | |
|---|---|---|
| DE | 2006126 | 2/1970 |
| DE | 3012849 | 10/1981 |
| DE | 3409061 | 4/1985 |

* cited by examiner

Primary Examiner—Brian Sircus
Assistant Examiner—Brian S. Webb
(74) Attorney, Agent, or Firm—Volpe and Koenig, P.C.

(57) ABSTRACT

A connecting plug (1) for a bipolar coagulation instrument having an insulating body (3) for mechanically combining and electrically separating and insulating both of its blades (2) or electrical connecting lugs is provided. The blades (2) have holes (7) in the interior of the insulating body (3) at a point at which the insulating body (3) itself has holes (6), the holes (6) in the insulating body (3) and the holes (7) in the blades (2) lying superimposed in each case so that anchoring elements (8) can in each case jointly penetrate these holes (6, 7) and can thus immobilize the blades (2) against shifting in their openings (5) in insulating body (3). In this way, a mechanical securing of the blades is obtained. Both holes (6) in the insulating body (3) can be blind holes and end at a distance from each other, which combines good positive mechanical immobilization of the blades (2) with an improved insulating effect.

15 Claims, 1 Drawing Sheet

CONNECTING PLUG FOR A MEDICAL BIPOLAR COAGULATION INSTRUMENT

BACKGROUND

The present invention concerns a connecting plug for a medical bipolar coagulation instrument, for example, for a bipolar coagulation pincette or for a bipolar electrode, with two blades separated at the ends by insulating material and joined by an insulating body, the blades exhibiting or forming electrical connectors, especially electrical connecting lugs, beyond the range over which they are joined together and the insulating body surrounding and running between the blades and exhibiting for this purpose longitudinally oriented openings for receiving or insertion of the blades.

DE-PS 2,006,126 discloses a coagulation pincette with a connecting plug of this type, the insulating body being formed as an injection-molded plastic part. The blades, due to the one-piece combination of this coagulation pincette with its connecting plug, need to be held by this insulating body spaced and insulated from each other. Thus, the insulating body simultaneously has a securing function in addition to its insulating function. It is therefore necessary to design this insulating body to be relatively bulky, which is a hindrance in handling especially because the end of the pincette is consequently relatively unwieldy and heavy, which is undesired, for example, in microsurgery. In spite of this bulky design, which is necessary for sufficient mechanical strength, one can not exclude the possibility that the blades will loosen with time due to movement and various thermal stresses occurring especially during sterilization so that the pincette becomes useless.

From DE-PS 30 12 849 a bipolar coagulation pincette with a connecting plug of the type mentioned above is known, in which the blades with the electrical connectors are inserted in two plastic shells and these are then held together by a sheath. Thus, the insulating body mainly has the function of a spacer and insulator while the outer sheath surrounds this insulating body in pressing and stabilizing fashion. The result is a stable joining of the blades which remains unchanged over a longer period of use. In addition, the outer dimensions can be reduced. Accordingly, this solution has become widespread even though it causes high production costs due to the manufacture of individual parts and their assembly. Beyond this, this arrangement is also subject to thermal stressing during sterilization so that different coefficients of expansion together with alternating bending loads during use as a result of opening and closing the pincette can lead to a gradual loosening.

From DE 34 09 061 C1 a bipolar coagulation instrument with a plug of the type mentioned above is known, which corresponds essentially to that provided by DE-PS 30 12 849, the insulating body being divided in two. A seam between the two parts of this insulating body—as in the coagulation pincette according to DE-PS 30 12 849—can not be avoided or can only be avoided through mutual gluing so that moisture can penetrate over the course of time.

The problem therefore exists of providing a connecting plug for a bipolar coagulation instrument of the type mentioned above, in which reliable securing of the blades in relation to the insulating body is made possible, a long service life of the joining of the blades is obtained, and production is economical. Nevertheless, seamless insulation of the two blades in the area of the insulating body should be simultaneously possible.

SUMMARY

In solving this problem, the above-mentioned connecting plug for a bipolar coagulation instrument or, in the case of a one-piece design of the instrument and the plug, the bipolar coagulation instrument is characterized by the fact that the insulating body and the blades each have holes which are superimposed in the installed position and by the fact that anchoring elements are provided which pass through these holes and penetrate in each case in the installed position at least some of the superimposed holes in the insulating body and the blades. Holes that open toward both sides are provided in the insulating body in which the anchoring elements that penetrate into the holes in the blades fit and are inserted in the installed position.

Thus, one can provide a preferably one-piece insulating body with passageways or openings for insertion of the blades—in the case of a bipolar coagulation pincette with onepiece connecting plug, the pincette blades—which is mechanically fixed in the installed position over against the inserted blades or pincette blades by anchoring elements oriented perpendicularly to the direction of pressing or insertion so that, compared to gluing or jamming, mechanically interlocking anchoring results, a continuous and seamless section of the insulating body, however, simultaneously extending between the blades so that no liquid or the like can penetrate in this area and can be brought to boiling or evaporation under the influence of high-frequency energy. Although the anchoring elements are to be inserted in each case from the side into the insulating body and are to be inserted into the holes of the blades, one obtains an arrangement which is relatively simple to manufacture and assemble, but which has the great advantage of a mechanically interlocking joining of the essential parts with each other, namely, the blades and the insulating body. Gluing, which can fail under the thermal stressing of sterilization, can be additionally present, to be sure, but is not necessary for the mutual immobilization against undesired shifts and loosenings.

The two holes in the insulating body can be formed as blind holes or borings and end at a distance from each other. Thus, no liquid can penetrate into the area between these holes; rather, the best possible insulating effect is attained at this point.

The holes can enter the insulating body on opposite sides, align with each other, and run perpendicular to the openings in the blades. This represents a simple arrangement of the holes in the insulating body, which additionally permits the best possible anchoring of the inserted blades.

The holes in the insulating body can open into the openings for the blades or cross these, and the anchoring elements can be located in the installed position with their inwardly lying face flush with the inside of the blades penetrated by them or project beyond the blades. In both alternative cases, the blades are engaged over their entire thickness by the anchoring elements. Since the blades are spaced from each other, the holes and accordingly the anchoring elements can cross the openings and thus also the blades, i.e., even protrude beyond these somewhat on the inside so that the anchoring elements in each case are supported to a certain extent bilaterally in relation to the blades held by them. The mechanical immobilization of the blades within the insulating body is all the more stable and secure in their longitudinal direction.

For the tightest possible arrangement and a strong union, it is appropriate if the anchoring elements have the same cross-section or external contour as the holes and fill these in the installed position over the entire length or depth of the holes and over the thickness of the blades. The anchoring elements then sit practically free of play in the holes so that a correspondingly strong union is produced. At the same time, they close the holes to the entrance of moisture.

The anchoring elements can consist of insulating material, especially of the same material as the insulating body. Thus, they can contact the blades on the inside in the area of their holes without the user needing to avoid contact with the two anchoring elements on the outside of the insulating body or the anchoring elements needing to be insulated on the outside. By using the same material for the anchoring elements and the insulating body, different coefficients of expansion are avoided.

The engageable holes in the blades for securing via the anchoring element can in each case be continuous, especially drilled through. To be sure, mechanical immobilization could also occur if the holes in the blades were not continuous so that the anchoring elements could penetrate only a portion of the thickness of the blades. However, a borehole is more easily produced and the mechanical strength of the joint using the anchoring elements is better if the elements penetrate the entire thickness of the blades or even jut out beyond the blade surface.

The end walls of the anchoring elements facing each other can be spaced from each other in the installed position. This spacing corresponds approximately to the distance which the blind holes in the insulating body have from each other so that a continuous layer of insulating-body insulating material remains in this area, in which, thus, no liquid can enter which unintentionally could be heated up by high-frequency energy under certain circumstances.

For good insulation, it is appropriate and advantageous here if the space between the end walls of the anchoring elements is at least partly and especially completely filled in by the material of the insulating body.

The anchoring elements can be fixed via frictional interlocking and jamming in the receiving holes and, if necessary, can even catch upon insertion into their holes through appropriate profiling. To be sure, this complicates production and assembly and is, under certain circumstances, not even an absolute guaranty against gradual loosening due to thermal and mechanical stressing and movement. It can therefore be expedient to secure (especially glue, heat-seal, or screw) the anchoring elements in the holes or borings receiving them. This has the additional advantage that the sealing against penetration of moisture or liquid is further improved.

Here, a further embodiment can provide that the anchoring elements have a cross-sectional reduction next to the blades, especially a groove running entirely or partially around their periphery for receiving primarily hardening synthetic resin or adhesive. The anchoring elements thus become fixed by this adhesive following its hardening.

The mutual joining of anchoring elements, blades, and the insulating body can be further improved through the fact that the openings for insertion of the blades in the insulating body are, compared to the blade dimensions, enlarged or expanded (possibly conically expanded) on at least one side especially against the insertion direction of the blades. The holes for the anchoring elements are positioned running perpendicular to these openings in this expanded area or at the transition from the expanded to the nonexpanded area. This not only facilitates the introduction or insertion of the blades into the openings in the insulating body and gives the blades better freedom of movement at their point of exit from the insulating body in the direction toward the working ends, but additionally permits the glue provided in the area of the anchoring elements also to enter at least into portions of the openings and, in combination especially with the adhesive located in a groove of the involved anchoring element and directly bonded thereto, improves the form-interlockingjoint to keep the anchoring element from being removed or falling out. For this purpose, it is useful if the expanded area of the openings extends to the anchoring elements and the part of the elements exhibiting a cross-sectional reduction.

The openings in the insulating body, on the one hand, and the holes in the blades, on the other, are appropriately of equal size, have identical contours, and are arranged congruently in the installed position and penetrated by the anchoring elements especially in congruent fashion over their entire cross-section. This produces a stable, positive, frictional joint which excludes loosening, can withstand high thermal stressing, and, however, simultaneously has a good insulating effect and can prevent the penetration of liquid between the insulated blades so that no undesired heating can occur there under the influence of high-frequency energy.

An arrangement further simplified with respect to fabrication can consist in the fact that the openings in the insulating body run or open into each other while the anchoring elements are particularly joined together as one piece into a continuous anchoring element. This permits combining the advantages of good mutual mechanical attachment with simplification of manufacture because a continuous hole for one or two anchoring elements is simpler to produce than two blind holes. With good tight filling of the holes by the anchoring element and possibly additional gluing, one nevertheless also obtains satisfactory insulation and sealing.

The insulating body can have a larger cross-section or diameter in the area of the holes for the anchoring element(s) than in the neighboring region of this insulating body extending in the direction of the electrical connectors, and this area of larger cross-section can serve as a stop for a plug mountable on the electrical connectors. Thus, one obtains an additional function for the insulating body because it can guide the plug and produces a specific insertion depth of the terminals to be joined together. The user only needs to insert the plug up to this stop in order to produce a reliable electrical connection. Thus, one also obtains a control for this electrical plug-type connection.

Above all upon combination of individual or several of the above-described features and measures, one obtains a connecting plug for a bipolar coagulation instrument, in particular, joined as one piece with the latter, for example, for a coagulation pincette in which the danger of premature loosening and thus sliding out of one or both blades (in the case of the coagulation pincette, the pincette blades) from the insulating body is avoided by an additional mechanical safety mechanism. Through additional gluing, any remaining seams or small openings can be closed, and the anchoring elements designed as cross pins can be immobilized and secured. At the same time, one attains a situation where no liquid can penetrate into the insulating body or the compound unit formed by it.

BRIEF DESCRIPTION OF THE DRAWINGS

Described in more detail below is a preferred embodiment of the present invention which is shown in the drawings. In the drawings.

DETAILED DESCRIPTION OF THE PREFERRED EMBODIMENT

Figure 1:
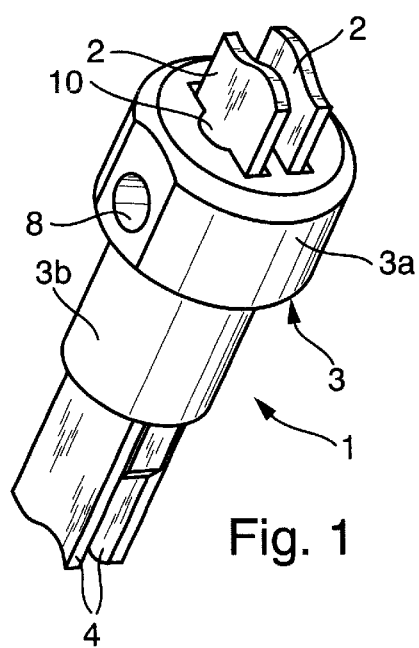
FIG. 1 is a perspective representation of a connecting plug for a bipolar coagulation pincette with blades held at their ends by an insulating body and separated electrically from each other, the blades as well as the electrical connecting lugs protruding on the opposite end being represented in truncated fashion, i.e., only partially.
Figure 3:
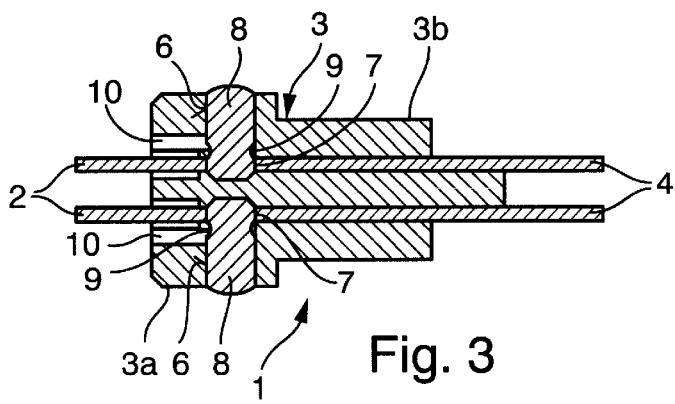
FIG. 3 is a longitudinal section view through the pincette in the area of attachment of the blades along line III—III in FIG. 4 and corresponding to the longitudinal section shown in FIG. 2, the blades and the anchoring elements now being inserted and shown.
Figure 4:
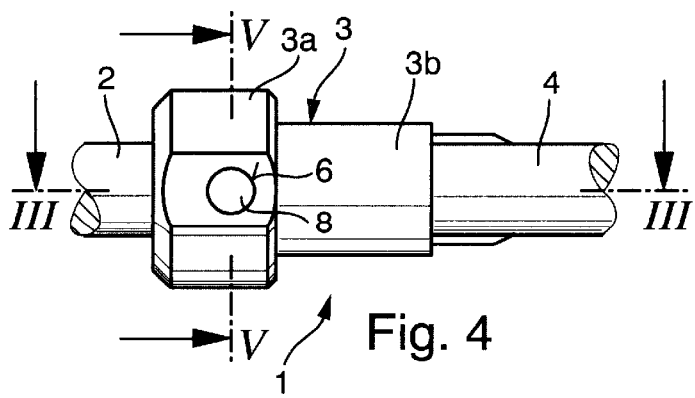
FIG. 4 is a lateral view of the coagulation pincette with a view of a hole or an anchoring element inserted therein, the blades and the electrical connecting lugs joined as one piece therewith again being shown in truncated or abbreviated form.

A connecting plug for a medical bipolar coagulation instrument (in the present embodiment, for a bipolar coagulation pincette), designated as a whole with 1, includes two blades 2 separated at their ends by insulating material, the ends being represented in FIGS. 1, 3, and 4 in abbreviated or truncated fashion. These blades 2 are joined together in the installed position by an insulating body, designated as a whole with 3, and are simultaneously insulated from each other.

Since, in the present embodiment, the connecting plug 1 is joined as one piece with the bipolar coagulation pincette, i.e., the pincette is part of the connecting plug 1 and the connecting plug is part of the pincette, it is also referred to in the following as "pincette 1". In addition, the blades 2 are referred to in the following as "pincette blades 2" while, in a differently designed bipolar coagulation instrument, for example, of the type shown in DE 34 09 031 C1, the blades could serve as electrical lugs.

Viewed from the unrepresented operating tips of the pincette 1 behind the assembled section and accordingly behind the insulating body 3, the blades 2 have electrical connectors, namely electrical connecting lugs 4, which in the present embodiment are formed by continuations of the blades through insulating body 3 and are combined as one piece with blades 2.

Figure 2:
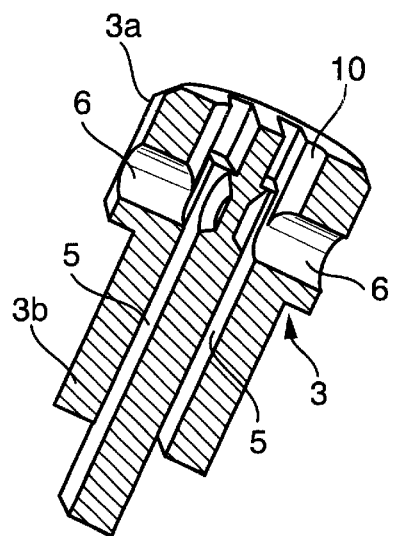
FIG. 2 is a perspective representation of a longitudinal section through the insulating body and thus simultaneously also through holes running perpendicular to the insulating body in which the anchoring elements that serve to secure the blades (not shown in FIG. 2) fit.

On the basis of FIGS. 1 and 3, it can be recognized that the insulating body 3 surrounds the blades 2 and runs between them. FIG. 2 shows that the insulating body has for this purpose openings 5 oriented in the longitudinal direction of the pincette 1 and having the form of slits for receiving or insertion of the blades 2. In the case of a one-piece insulating body 3, the blades 2 can be introduced and inserted into the openings 5 from one of the end faces.

Figure 5:
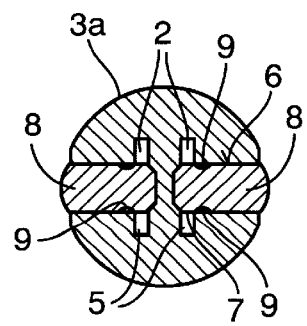
FIG. 5 is a cross-sectional view through the coagulation pincette in the area of the blade-securing insulation body along line V—V of FIG. 4.

It is clear in FIGS. 3 and 5 that the insulating body 3 and the blades 2 each have holes 6 and 7 aligned in the installed position and that anchoring elements 8 are provided which fit in the holes 6 and 7, and in the installed position each penetrate through these aligned holes 6 in the insulating body 3 and the holes 7 in the blades 2. Here, it will be recognized in the mentioned FIGS. 3 and 5, but especially well also in FIG. 2, that the insulating body 3 is provided with holes 6 that open toward both sides in which the anchoring elements 8 engaging into the holes 7 of blades 2 fit, with the elements being inserted in the installed position as shown in FIGS. 3 and 5. It is clear that longitudinal shifting of the pincette blades 2 within the openings 5 is thus no longer possible, i.e., the blades 2 and the insulating body 3 are immobilized with respect to each other. Here, the anchoring elements 8 end at the surface of the insulating body 3.

According to FIGS. 2, 3, and 5, both of the holes 6 in the insulating body 3 are designed as blind holes or borings and end in the interior of insulating the body 3 at a distance from each other so that insulating material of the insulating body 3 is located between their interior bottom or end walls, which produces good mutual insulation of the blades 2 in this area, too. Holes 6 enter here into the insulating body 3 on diametrically opposed sides, are aligned with each other, and run across, in the present embodiment, at a right angle to, the openings 5 for blades 2 so that they can include the blade holes 7 in their course.

The holes 6 in insulating body 3 thus open into the openings 5 for blades 2 and even cross these according to the present embodiment so that the anchoring elements 8 protrude inwardly somewhat beyond the blades 2 which they penetrate in the installed position, as FIGS. 3 and 5 show. The interior end walls of the anchoring elements 8 are thus a somewhat shorter distance from each other than the flat blades 2 running parallel to each other. As a result, the anchoring elements 8 are held and secured by the insulating body 3 on both sides of the blades 2 or the continuing electrical connecting lugs 4 so that they can also accommodate correspondingly high shearing forces. Here, the anchoring elements 8 have the same cross-sectional shape or outer contour as the holes 6 and 7 and fill these in the installed position over their entire length and depth as well as over the thickness of the blades 2, which simultaneously leads to good sealing.

To be sure, the insulating body 3 already provides for sufficient insulation of blades 2 and electrical connecting lugs 4, the anchoring elements 8 can also be formed of insulating material and particularly of the same material as the insulating body 3. This improves the insulating effect and prevents different thermal movements of the anchoring elements 8 over against the insulating body 3.

The holes 7 are plugged in each case for securing purposes by the anchoring element 8 that are continuous or drilled through the blades 2, in order to permit the anchoring elements 8 to project on both sides.

It should be mentioned at this point that the holes 7 in blades 2 could, if necessary, also have a smaller cross-section than holes 6 in the insulating body 3 provided, namely, that anchoring elements 8 had a cross-sectional reduction or attenuation in the interior.

As a result of the above-prescribed measures, the facing end walls of the anchoring elements 8 are spaced from each other in the installed position, i.e., after insertion into the holes 6 and 7, the space being filled in by material of insulating body 3. As a result, seams which could link together the openings 5 for blades 2 are avoided with certainty, i.e., blades 2 are not only insulated from each other within insulating body 3, but are also sealed off.

Although stable mounting can already be attained through jamming or light press-fitting of the anchoring elements in holes 6, anchoring elements 8 can be additionally secured in their receiving holes 6 or borings, for example, glued, heat-sealed, or, upon introduction of threads, screwed. As a result, the sealing effect is simultaneously further improved.

In FIGS. 3 and 5, it is indicated that the anchoring elements 8 have a cross-sectional reduction adjacent to the blades 2, in the present embodiment, a groove 9 on their periphery for accommodating especially a hardening adhesive. At the same time, it can be seen from FIGS. 2 and 3 that the openings 5 for the blades 2 are enlarged or expanded compared to the dimensions of the blades 2 on at least one side, in the present embodiment, on the side of the blades 2 opposite the electrical connecting lugs 4 and in particular counter to the direction of insertion of the blades 2, this not needing to be the case according to FIG. 1 over the entire breadth of the blades 2 or electrical connecting lugs 4. The holes 6 for the anchoring elements 8 are positioned running perpendicularly in this expanded range 10 or at the transition from this expanded range 10 to the nonexpanded range of openings 5. This is particularly clearly in FIG. 3, where expanded range 10 extends up to the one side of anchoring elements 8 and into the area of groove 9. Thus, adhesive can be subsequently supplied via this expanded range 10, the adhesive then also fills up the cross-sectional reduction or groove 9 and after hardening forms a locking structure for the anchoring element 8 counter to its insertion direction and thus additionally immobilizing the anchoring element 8.

The result overall is that the holes 6 in the insulating body 3 and the holes 7 in the blades 2 or in the electrical connecting lugs 4 are the same size, have coinciding contours, and are congruent in the installed position and penetrated by the anchoring elements 8. As mentioned, however, stepped anchoring elements 8 with smaller cross-sections in the interior could be provided if the holes 7 in the blades 2 were smaller than the holes 6.

A modified embodiment (not shown) could provide that the holes 6 in the insulating body 3 not only align, but also pass over into each other, with the anchoring elements 8 being combined as one piece into a continuous anchoring element. As a result, assembly could be facilitated.

It will be further recognized from FIGS. 1–4 that the insulating body 3 has a larger cross-section or diameter in the area 3a of the perpendicularly running holes 6 for the anchoring element(s) 8 than the adjacent area 3b extending in the direction of the electrical connecting lugs 4 so that this first-mentioned area 3a protrudes radially compared to adjacent area 3b and can serve as a stop for an unshown plug mountable on the electrical connectors 4. As a result, the insulating body 3 thus obtains an additional function. In addition, it will be recognized that the insulating body is lengthened in the area between the electrical connecting lugs 4 beyond the area 3b in order to maintain the spacing of the electrical connectors 4 over part of their range outside of the insulating body 3.

The connecting plug 1 for a bipolar coagulation instrument exhibits an insulating body 3 for mechanically combining and electrically separating and insulating both of its blades 2 or electrical connecting lugs. The blades 2 have holes 7 in the interior of the insulating body 3 at a point at which the insulating body 3 itself has holes 6, the holes 6 in the insulating body 3 and the holes 7 in the blades 2 lying superimposed in each case so that the anchoring elements 8 can in each case jointly penetrate these holes 6 and 7 and can thus immobilize blades 2 against shifting in their openings 5 in the insulating body 3. In this way, a mechanical securing of the blades is obtained. Both holes 6 in the insulating body 3 can be blind holes and end at a distance from each other, which combines good positive mechanical immobilization of blades 2 with an improved insulating effect.

What is claimed is:

1. Connecting plug (1) for a medical bipolar coagulation instrument comprising two blades (2) having ends separated by insulating material and joined by an insulating body (3), the blades including or forming electrical connecting projections (4) or lugs that extend beyond an area over which the blades are joined together, the insulating body (3) surrounding and extending between the blades (2) and including openings (5) oriented in a longitudinal direction of the instrument (1) for receiving or insertion of the blades (2), the insulating body (3) and the blades (2) each have holes (6, 7) which are superimposed in an installed position and anchoring elements (8) pass through the holes (6, 7) and penetrate in each case in the installed position at least a portion of the superimposed holes (6, 7) in the insulating body (3) and the blades (2), the anchoring elements (8) pass through the holes (6) that open toward both sides of the insulating body (3) and penetrate into the holes (7) in the blades (2) in the installed position, the anchoring elements (8) have a cross-sectional reduction next to the blades (2) comprising a groove (9) running entirely or partially around their periphery for receiving a hardening adhesive.

2. Connecting plug according to claim 1, wherein the two holes (6) in the insulating body (3) are designed as blind holes or borings and end spaced apart a distance from each other.

3. Connecting plug according to claim 1, wherein the holes (6) in the insulating body (3) enter on opposing sides, aligned with each other, and run perpendicular to the openings (5) for the blades (2).

4. Connecting plug according to claim 1, wherein the holes (6) in the insulating body (3) open into or cross the openings (5) for the blades (2), and the anchoring elements (8) are located in the installed position with their inwardly lying face flush with or project beyond an inside of the penetrated blades (2).

5. Connecting plug according to claim 1, wherein the anchoring elements (8) have a cross-section or external contour that is the same as the holes (6, 7) and fill the holes in the installed position over the entire length or depth of the holes and over a thickness of the blades (2).

6. Connecting plug according to claim 1, wherein the anchoring elements (8) are formed of insulating material.

7. Connecting plug according to claim 6, wherein the anchoring elements (8) are formed of the same material as the insulating body (3).

8. Connecting plug according to claim 1, wherein the engageable holes (7) in the blades (2) for securing by the anchoring element (8) are continuous.

9. Connecting plug according to claim 1, wherein end walls of the anchoring elements (8) face each other and are spaced from each other in the installed position.

10. Connecting plug according to claim 1, wherein a space between end walls of the anchoring elements is at least partly filled in by material of the insulating body (3).

11. Connecting plug according to claim 1, wherein the holes (6) in the insulating body (3), on the one hand, and the holes (7) in the blades (2), on the other, are of equal size, have identical contours, and are arranged congruently in the installed position and penetrated by the anchoring elements (8).

12. Connecting plug according to claim 1, wherein the holes (6) in the insulating body (3) extend into each other and the anchoring elements (8) are joined together as one piece into a continuous anchoring element.

13. Connecting plug according to claim 1, wherein the insulating body (3) has a larger cross-section or diameter in an area (3a) of the holes (6) for the anchoring element(s) (8) than in a neighboring region (3b) extending in a direction of the electrical connectors (4) and serves as a stop for a plug mountable on the electrical connectors (4).

14. Connecting plug (1) for a medical bipolar coagulation instrument comprising two blades (2) having ends separated by insulating material and joined by an insulating body (3), the blades including or forming electrical connecting projections (4) or lugs that extend beyond an area over which the blades are joined together, the insulating body (3) surrounding and extending between the blades (2) and including openings (5) oriented in a longitudinal direction of the instrument (1) for receiving or insertion of the blades (2), the insulating body (3) and the blades (2) each have holes (6, 7) which are superimposed in an installed position and anchoring elements (8) pass through the holes (6, 7) and penetrate in each case in the installed position at least a portion of the superimposed holes (6, 7) in the insulating body (3) and the blades (2), the anchoring elements (8) pass through the holes (6) that open toward both sides of the insulating body (3) and penetrate into the holes (7) in the blades (2) in the installed position, the openings (5) for the blades (2) are enlarged or expanded in an expanded range compared to a dimension of the blades (2) at least on one side, especially against an insertion direction of the blades (2), and the holes (6) for the anchoring elements (8) are positioned perpendicular to the blade openings in the expanded range (10) or at a transition from the expanded range (10) to a nonexpanded area of the openings (5) the expanded range (10) of the openings (5) extends to the anchoring elements (8) and a part of the anchoring elements exhibiting a cross-sectional reduction.

15. Connecting plug according to claim 14, wherein the anchoring elements (8) are secured in the holes (6) by at least one of glue, heat-sealing, or screws.

* * * * *